(12) United States Patent
Maschke

(10) Patent No.: US 9,039,282 B2
(45) Date of Patent: May 26, 2015

(54) IMAGING APPARATUS COMPRISING A RING-SHAPED GANTRY

(75) Inventor: Michael Maschke, Lonnerstadt (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 753 days.

(21) Appl. No.: 13/105,017

(22) Filed: May 11, 2011

(65) Prior Publication Data

US 2011/0280380 A1    Nov. 17, 2011

(30) Foreign Application Priority Data

May 14, 2010   (DE) .......................... 10 2010 020 604

(51) Int. Cl.
*H05G 1/02* (2006.01)
*A61B 6/00* (2006.01)

(52) U.S. Cl.
CPC ............. *A61B 6/4411* (2013.01); *A61B 6/4435* (2013.01); *A61B 6/4458* (2013.01)

(58) Field of Classification Search
CPC .... A61B 6/035; A61B 6/4435; A61B 6/4458; A61B 6/4464
USPC ................. 378/196, 197, 198, 9, 10
See application file for complete search history.

(56) References Cited

U.S. PATENT DOCUMENTS

| | | | | |
|---|---|---|---|---|
| 3,373,285 A | * | 3/1968 | Barrett ........................... | 378/194 |
| 4,220,863 A | * | 9/1980 | McBride et al. ................ | 378/10 |
| 4,747,119 A | * | 5/1988 | Heinz et al. .................... | 378/197 |
| 5,014,293 A | * | 5/1991 | Boyd et al. ..................... | 378/197 |
| 5,048,070 A | * | 9/1991 | Maehama et al. ............. | 378/197 |
| 5,095,501 A | * | 3/1992 | Kobayashi ...................... | 378/196 |
| 6,385,292 B1 | * | 5/2002 | Dunham et al. ............... | 378/122 |
| 6,461,039 B1 | * | 10/2002 | Klotz et al. .................... | 378/197 |
| 6,940,941 B2 | | 9/2005 | Grant | |
| 7,263,157 B2 | | 8/2007 | Bruder | |
| 7,359,484 B2 | | 4/2008 | Lu | |
| 8,457,279 B2 | * | 6/2013 | Saracen et al. ................. | 378/69 |

(Continued)

FOREIGN PATENT DOCUMENTS

| | | |
|---|---|---|
| DE | 19802405 B4 | 7/2004 |
| DE | 102006051475 A1 | 5/2008 |
| DE | 60223179 T2 | 8/2008 |
| DE | 102007033716 A1 | 1/2009 |

OTHER PUBLICATIONS

Siemens AG, Healthcare Sector; Artis zee, Advanced applications in interventional radiology, www.siemens.com/healthcare; Order No. A91AX-20822-12C1-766, Printed in Germany; © Jan. 2009; pp. 1-14.

(Continued)

*Primary Examiner* — Glen Kao

(57) ABSTRACT

An imaging apparatus having a ring-shaped gantry is provided. The gantry has a rotor arrangement rotating therein and a radiation source as well as at least one radiation detector. The gantry has at least one gantry segment which can be detached from the ring shape to allow the gantry to be opened laterally. The gantry is arranged on a supporting structure so as to be movable in space. The supporting structure is a ceiling-mounted stand having at least two degrees of freedom of movement. The gantry has at least two radiation sources disposed offset by an angle on the rotor arrangement and associated with each of which is at least one radiation detector.

13 Claims, 3 Drawing Sheets

(56) References Cited

U.S. PATENT DOCUMENTS

| | | | |
|---|---|---|---|
| 2004/0022350 A1* | 2/2004 | Gregerson et al. | 378/15 |
| 2005/0129181 A1* | 6/2005 | Shinoda | 378/209 |
| 2006/0120507 A1 | 6/2006 | Brunner | |
| 2006/0171508 A1* | 8/2006 | Noda et al. | 378/193 |
| 2006/0285643 A1* | 12/2006 | Molz et al. | 378/101 |
| 2008/0130829 A1* | 6/2008 | Bruder et al. | 378/9 |
| 2008/0159485 A1* | 7/2008 | Ye | 378/167 |
| 2009/0028290 A1* | 1/2009 | Grebner et al. | 378/9 |

OTHER PUBLICATIONS

Data sheet: Artis zee; Ceiling-mounted system for surgical angiography, Siemens AG Medical Solutions; www.siemens.com/healthcare, Aug. 2008; pp. 1- 28; Order No. A91AX-20805-31T1-7600; Printed in Germany.

Medtronic Navigation, Inc.; O-arm® Multi-dimensional Surgical Imaging System 9670939 Rev 2 (Feb. 2011); pp. 1-22.

* cited by examiner

IMAGING APPARATUS COMPRISING A RING-SHAPED GANTRY

CROSS REFERENCE TO RELATED APPLICATIONS

This application claims priority of German application No. 10 2010 020 604.0 filed May 14, 2010, which is incorporated by reference herein in its entirety.

FIELD OF THE INVENTION

The invention relates to an imaging apparatus comprising a ring-shaped gantry having a rotor arrangement rotating therein and having an image acquisition means comprising a radiation source as well as at least one radiation detector, wherein the gantry having at least one gantry segment which can be detached from the ring shape to allow the gantry to be opened laterally is arranged on a supporting structure so as to be movable in space.

BACKGROUND OF THE INVENTION

Minimally invasive interventions and minimally surgical interventional procedures on patients are increasingly replacing traditional surgical operations. A factor of crucial importance in this regard is good anatomical and functional medical imaging, in particular of soft tissue, in the case of interventions involving the heart and liver for example. For this purpose use is predominantly made of X-ray devices for acquiring fluoroscopic images, said devices possessing a certain mobility to enable the image acquisition means to be positioned as appropriate in order to permit the intervention that is being performed in parallel. Mobile C-arm X-ray machines are known in which a radiation source and a radiation detector are arranged at the ends of a C-arm, said C-arm having the ability to be moved in space and positioned relative to the patient or, as the case may be, the treatment region. However, X-ray machines of this kind generally provide only 2D images and sometimes the soft-tissue resolution is unsatisfactory or the image quality is not such that sufficient information can be acquired in particular in the case of complex interventions.

Improved image acquisition, including with regard to three-dimensional imaging, is possible by means of an imaging apparatus comprising a ring-shaped gantry, i.e. a mobile computed tomography (CT) scanner or a mobile computed tomography gantry which is arranged on a supporting structure such as a mobile cart which can travel across a floor for example, as described by way of example in U.S. Pat. No. 6,940,941. By means of such a mobile CT scanner, in the gantry of which there rotates a rotating rotor arrangement having an image acquisition means comprising a radiation source and, for example, a radiation detector arranged offset by 180° therefrom, i.e. disposed opposite thereto, images can be recorded continuously during the treatment owing to the continuous rotation of the rotor arrangement, thereby resulting in very good soft-tissue resolution within the acquired images, and consequently in very good image quality. Also provided in the case of the gantry known from U.S. Pat. No. 6,940,941 is a detachable or breakable gantry segment, which is to say that the gantry can be opened laterally, thus enabling the patient to be introduced into the gantry from the lateral direction.

However, a disadvantage of the known mobile gantry is to be seen in the fact that e.g. the mobile cart on which the gantry is arranged takes up a considerable amount of space which is then no longer available for positioning other equipment required for a treatment or in which it is also not possible for persons involved in the treatment to remain.

In particular in computed tomography examinations of the heart it is furthermore only possible to record an entire cardiac cycle using an image acquisition means having a rotating radiation source when the heart rate is reduced to 60 bpm or less with the aid of suitable drugs, beta blockers for example. This is disadvantageous for the patient on the one hand, and on the other hand optimal image acquisition is not always assured, especially at somewhat slower rotational speeds.

SUMMARY OF THE INVENTION

The problem underlying the invention is therefore to improve an imaging apparatus of the type cited in the introduction in terms of its accessibility and also in terms of the quality of the imaging.

In order to solve this problem it is provided according to the invention in the case of an imaging apparatus of the type cited in the introduction that the supporting structure is a ceiling-mounted stand having at least two degrees of freedom of movement, wherein there are provided in the gantry at least two radiation sources disposed offset by an angle on the rotor arrangement and associated with each of which is at least one radiation detector.

According to the invention the openable gantry is arranged on a stand secured to the ceiling, i.e. it is guided from above. A transport cart that is movable across the floor or a similar contrivance is no longer provided according to the invention, thereby consequently considerably improving the accessibility of the gantry both with regard to the positioning of any equipment and for people as well as with regard to the possibility of easily positioning the patient.

The gantry is also characterized by the use of two radiation sources which are disposed offset by a defined angle from each other in or on the rotor arrangement. By means of said two radiation sources in conjunction with the associated detectors it is possible to record images at twice as high a heart rate or, as the case may be, to record a complete cardiac cycle in full even at the normal heart rate. Toward that end the two radiation sources are operated in parallel, the detectors continuously providing parallel images, though from different projection directions. As a result of this it is no longer absolutely necessary to administer any drugs to slow the heart rate on the one hand, while on the other hand high-quality images of a moving organ can be recorded even at somewhat lower rotational speeds.

In order to enable adequate freedom of movement and as a result thereof positioning freedom of the gantry it is already sufficient if the stand has at least two degrees of freedom of movement. An improvement in the freedom of movement or, as the case may be, positioning capability is given if more degrees of freedom are provided, for which reason the gantry is beneficially movable linearly by way of the stand along at least one horizontal axis, preferably two horizontal axes standing orthogonally relative to each other, and a vertical axis and in addition is rotatably mounted on the stand via a revolute joint having at least one degree of rotational freedom. For example, the stand can be moved linearly across the ceiling along two horizontal axes, i.e. in the x- and y-direction, and a further degree of freedom can be provided in a movement along the vertical z-axis. The gantry itself is coupled to the stand directly via a revolute joint which, for example, possesses one degree of rotational freedom about a horizontal axis, i.e. the x- or y-axis for example, but preferably can also be rotated about the z-axis. The movement of the stand along an axis or, as the case may be, the movement of the gantry on the stand is preferably effected by means of suitable motors which are arranged at the corresponding movement interfaces or engage there, although a manual movement is likewise conceivable. To control the movement a suitable control device is provided via which all of the motors are controlled, for example using a joystick or a similar control element.

As described, at least one radiation detector is associated with each of the two radiation sources. This can be implemented in such a way that two radiation detectors are also disposed on the rotor arrangement in addition to the two radiation sources and rotate with the rotor arrangement. The detectors are disposed opposite the respective radiation sources, in other words are positioned offset by 180°. Thus, two radiation source-radiation detector pairs are formed. Alternatively the assignment of the detectors can also be realized in such a way that a multiplicity of detectors are arranged in a stationary manner on the gantry, the detectors complementing one another to form a ring shape. In this case, therefore, the two radiation sources rotate relative to the positionally fixed radiation detectors such that each radiation source is associated with a multiplicity of detectors, ultimately with all of the detectors integrated in the detector ring.

Typical detectors used in the case of a computed tomography scanner are composed of a plurality of individual detectors. They possess good temporal resolution, though at a pixel size of approx. 400 µm sometimes have only a limited spatial resolution. Whereas two radiation sources are provided in the imaging apparatus according to the invention, it is provided according to a particularly advantageous development of the invention to use radiation detectors of different types, wherein one radiation detector is a known, conventional CT receiver consisting of a multiplicity of individual detectors and the other radiation detector is a planar solid-state radiation detector. Such a solid-state radiation detector possesses a considerably smaller pixel size of, for example, approx. 100 µm and hence a good spatial resolution, albeit a somewhat poorer temporal resolution. If two different radiation detectors are now used, the advantages of the respective receiver types can be exploited and at the same time the respective disadvantages compensated for. The solid-state radiation detector can be, for example, a detector based on amorphous silicon (aSi), a CMOS detector, a detector based on cadmium telluride (CdTe) or cadmium zinc telluride (CzT) or a detector based on organic photodiodes.

One radiation source is preferably a carbon nanotube emitter.

The rotor arrangement itself preferably extends through an angle of max. 270°, which is to say that the gantry can be opened with a segment describing at least 90°, although opening over a quadrant is also generally sufficient for positioning the patient.

In this case the rotor arrangement itself is embodied in such a way and/or the image acquisition means are disposed on the rotor arrangement in such a way that the two radiation sources are arranged offset by 90° from each other. The result of this, insofar as the detectors are disposed on the rotor arrangement, is that the detectors are likewise arranged offset by 90° from each other; overall, all elements of the image acquisition means are spaced 90° apart from one another. At the same time the rotor arrangement itself can extend through 270° and a radiation source or a radiation detector can be positioned at its ends. It is, however, also conceivable that the rotor arrangement extends through a smaller angle and the radiation source or the radiation detector is positioned so as to effectively lengthen the rotor arrangement. In any event a gantry segment extending through max. 90° can still be opened as before.

Furthermore a patient positioning table can be provided which can be moved translationally and/or rotationally in space. It can be adjusted manually or in a motor-driven manner in terms of its height, length and transverse direction, and can be fixed to the floor, wall or ceiling by way of a suitable supporting structure. An optional inclination in the x-, y- and/or z-direction is also possible, while the patient positioning table can also optionally rotate about a central point; a circular or elliptical rotational movement about a fixed point is also conceivable. In particular the use of an articulated-arm robot having at least four, preferably six, degrees of freedom is suitable for moving the patient positioning table, said articulated-arm robot, in particular if having six degrees of freedom, enabling translational and rotational movements in or about any spatial direction axis and consequently allowing an arbitrary positioning of the patient positioning table in space.

BRIEF DESCRIPTION OF THE DRAWINGS

Further advantages, features and details of the invention will emerge from the exemplary embodiment described below as well as with reference to the drawings, in which.

DETAILED DESCRIPTION OF THE INVENTION

Figure 1:
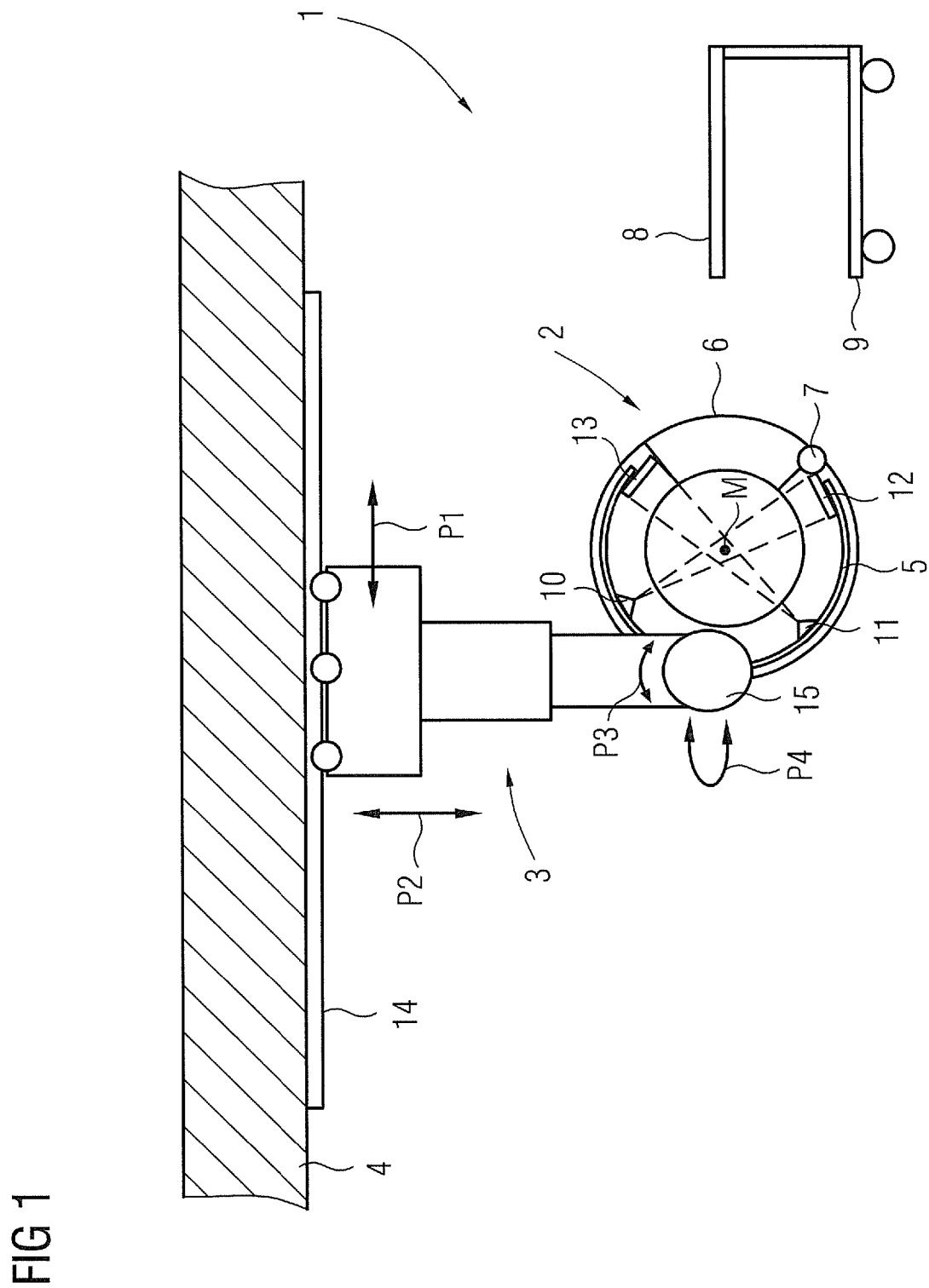
FIG. 1 is a schematic representation of an imaging apparatus according to the invention with closed gantry.

FIG. 1 shows in the form of a schematic diagram an imaging apparatus 1 according to the invention, comprising a gantry 2 which is arranged so as to be movable by way of a stand 3 on a ceiling 4. The gantry 2 comprises a rotor arrangement 5 which, driven by way of a motor, rotates about the center point M on runner rails (not shown in further detail) located inside the gantry 2. The rotor arrangement 5 extends through approx. 270°. This enables it to be brought into a park position in which a segment 6 of the gantry which is pivotably mounted by way of a hinge 7 can be swung open (see FIG. 2) so that the inside of the gantry 2 is accessible. It is now possible to position a patient (not shown in further detail) inside the gantry 2 by means of a patient positioning table 8 on which the patient is located and which in the example shown can be moved in space by way of a cart 9. Appropriate locking means (not shown in further detail) are of course provided for the purpose of fixing the rotor arrangement in position as well as for locking the segment 6 of the gantry 2.

In the example shown the rotor arrangement 5 carries two radiation sources 10, 11 which are X-ray tubes, preferably carbon nanotube emitters. The two radiation sources 10, 11 are spaced apart from each other by 90°. Disposed opposite each radiation source 10, 11 is a radiation detector 12, 13, these likewise being arranged spaced apart by 90° from the respective radiation source. In other words all four components are therefore spaced apart from one another by 90°. In this embodiment the radiation detectors 12, 13 co-rotate with the radiation sources 10, 11, i.e. two pairs made up of a radiation source and a radiation detector are fondled, namely the pair 10-12 and the pair 11-13. The radiation detectors 12, 13 can be of the same type, although preferably they are of different types. While the radiation detector 12 can be a conventional computed tomography detector consisting of a multiplicity of individual detectors arranged adjacent to one another, the radiation detector 13 can be for example a planar solid-state radiation detector based for example on aSi or similar.

The stand 3 itself is arranged on ceiling rails 14 and can be moved in at least one horizontal direction, as indicated by the double arrow P1. It is of course possible to realize an additional movability in a horizontal direction at right angles thereto, for which purpose a further movement plane would need to be provided.

Furthermore, the stand 3 is also movable vertically along the vertical axis, such that the gantry 2 can be varied not only in its horizontal position, but also in its vertical position. This is indicated by the double arrow P2.

The gantry 2 itself is rotatably mounted on the stand 3 via a revolute joint 15 which in the example shown possesses two degrees of rotational freedom. It can firstly be rotated about a horizontal axis, as indicated by the double arrow P3. This enables the gantry to be arranged on the other side of the stand also if need be, if the space conditions or type of examination make this necessary. The gantry 2 can furthermore be pivoted about the vertical axis, as indicated by the double arrow P4. This enables the gantry 2 to be rotated laterally. All in all, a virtually arbitrary positioning capability of the gantry 2 in space is realized by this means.

When a patient is to be examined the gantry 2 is first moved into the desired position in which it is possible to introduce the patient into the gantry. This is preferably accomplished automatically in that suitable motors are provided at the respective movement interfaces of the stand 3 or revolute joint 15 for the purpose of effecting the respective movement. This is controlled by the user by way of a central control device (not shown in further detail) for example with the aid of a joystick or similar. A hydraulic or pneumatic movement in the respective planes/axes would also be conceivable instead of a motorized movement.

After the transfer position has been reached a check is first made to determine whether the rotor arrangement 5 is in the rest or park position in order then, after locking the rotor arrangement 5 and opening the segment lock, to open the segment 6 of the gantry 2 and introduce the patient by way of the patient positioning table 8. After the patient has been positioned the segment 6 is then closed again, whereupon the examination can begin, in the course of which the rotor arrangement 5 rotates at high speed around the center M of the gantry 2. In the process both radiation sources 10, 11 are operated simultaneously, while images are also simultaneously and continuously recorded from the different fluoroscopic directions via both radiation detectors 12, 13, said images subsequently being processed in the control device (not shown in further detail), analyzed and displayed on a monitor.

Figure 3:
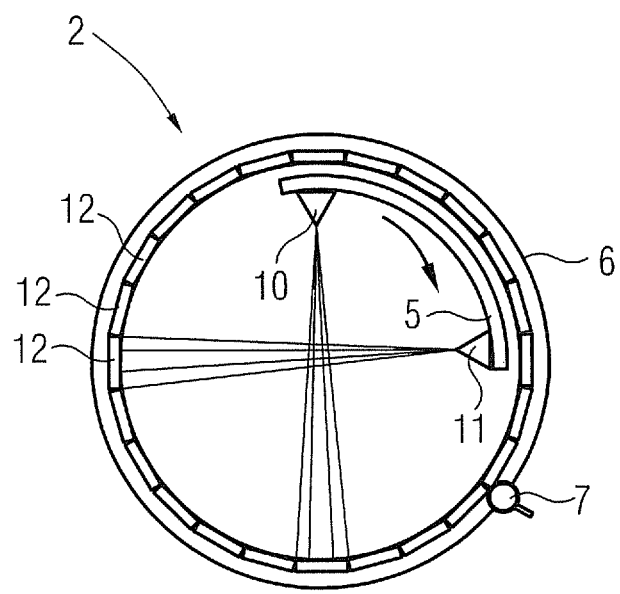
FIG. 3 is a schematic representation of a gantry having two rotating radiation sources and a multiplicity of stationary radiation detectors.
Figure 4:
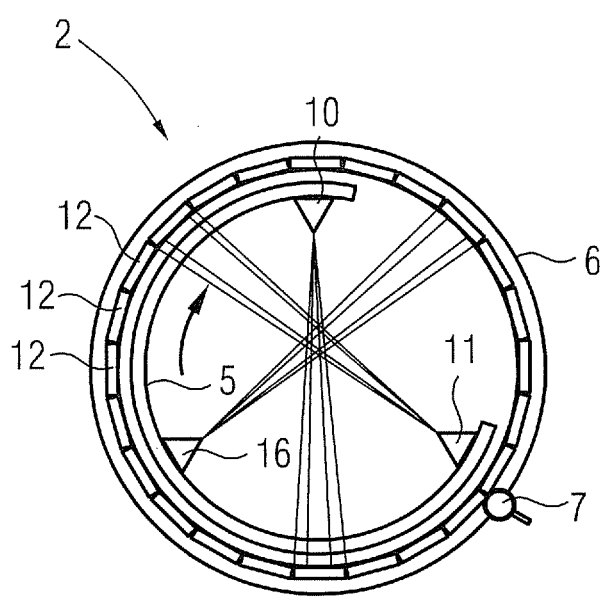
FIG. 4 is a schematic representation of a gantry having three rotating radiation sources and a multiplicity of stationary radiation detectors.

FIGS. 3 and 4 show in a schematic representation two further embodiment variants of a gantry 2 which again has a segment 6 which is pivotably mounted by way of a hinge 7 and allows the gantry 2 to be opened. At this point it should be noted that other movement mechanisms can, of course, also be provided for releasing the segment 6 from its ring position. For example, it can be removed completely by way of a suitable removal mechanism, while lifting it on a linear bearing and similar is also conceivable.

Here too a rotor arrangement 5 is provided which carries both radiation sources 10, 11, though not the radiation detectors, for which reason the rotor arrangement 5 in the example shown also only extends through somewhat more than 90°. The two radiation sources 10, 11 are spaced apart from each other by 90°. In this case also the rotor arrangement 5 runs on suitable guide rails (not shown) of the gantry 2, while a motor (likewise not shown) is in turn provided as a driving means.

Figure 2:
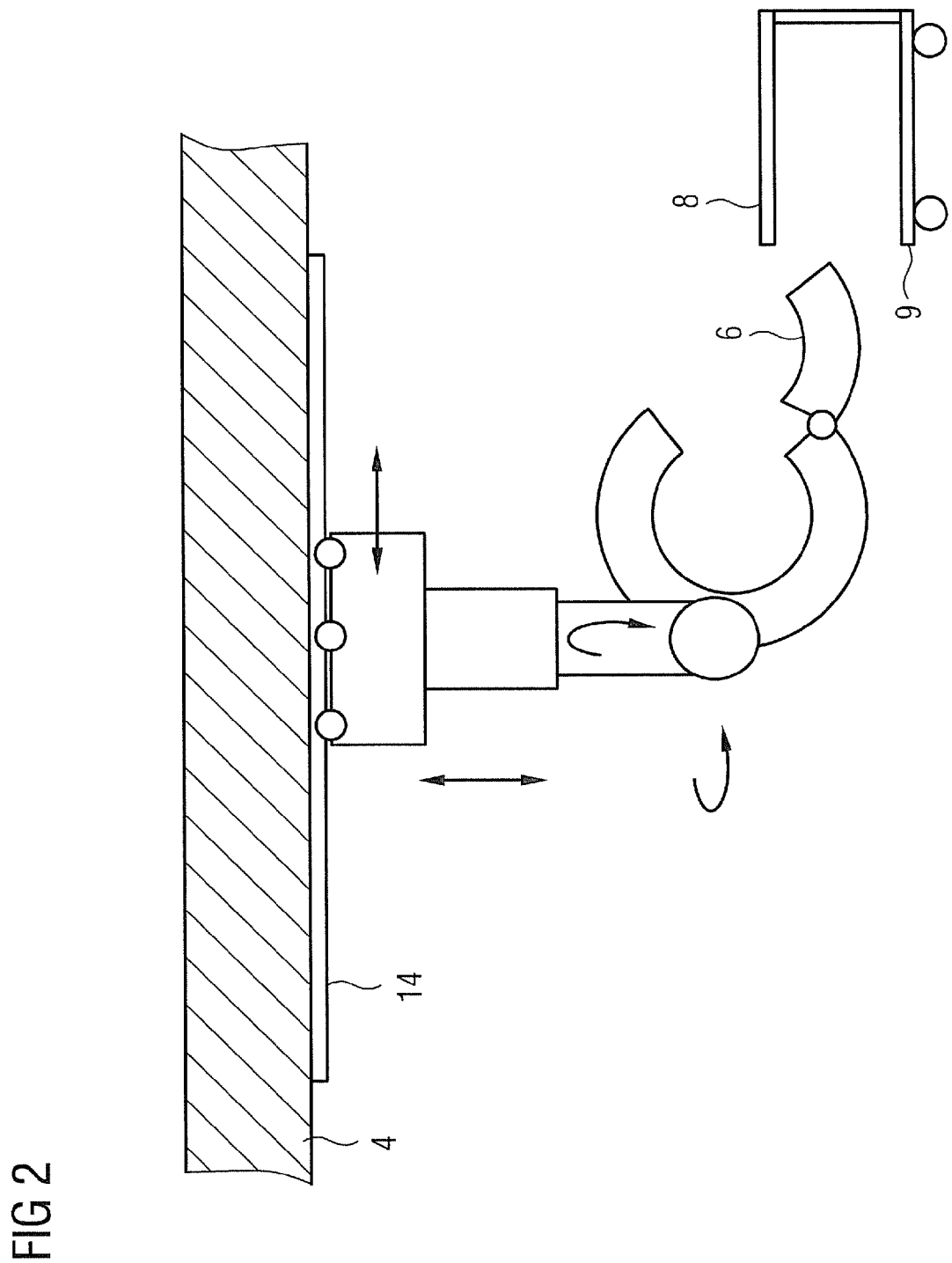
FIG. 2 shows the imaging apparatus from FIG. 1 with open gantry.

In contrast to the embodiments according to FIGS. 1 and 2, in this case a multiplicity of individual stationary radiation detectors 10 are provided which are arranged fixed in position on the gantry 2 and can be impinged upon by X-ray radiation from the respective radiation sources 10, 11. The radiation detectors 10 complement one another to create a ring shape, thus forming a complete, closed detector ring. It is possible to arrange radiation detectors of different types in two successive planes, i.e. one detector ring consisting of radiation detectors 12 in a first plane, for example, and a radiation detector ring consisting of radiation detectors 13 in a second, immediately contiguous plane, so that the advantageous properties of the different detector types can be used in this case too.

Finally, FIG. 4 shows an embodiment variant having three radiation sources 10, 11, 16 which are again arranged on a common rotor arrangement 5 which in turn extends through less than 270° around the inner circumference of the gantry 2. Here too stationary radiation detectors 12 or 13 arranged in a ring shape are again provided in one or two planes.

The invention claimed is:
1. An imaging apparatus, comprising:
  a ceiling-mounted stand having at least two degrees of freedom of movement; and
  a ring-shaped gantry arranged on the stand to be moved in space comprising:
    a rotor arrangement rotating in the gantry,
    at least two x-ray radiation sources disposed offset by an angle on the rotor arrangement, and
    at least two x-ray radiation detectors each associated with each of the x-ray radiation sources,
  wherein the gantry comprises at least one gantry segment which can be detached from the gantry to allow the gantry to be opened laterally, and
  wherein the gantry is rotatably mounted on the stand by a revolute joint having at least one degree of rotational freedom, and
  wherein the revolute joint is arranged such that the gantry is rotatable in a first direction and pivotable in a second direction different from the first direction about a common axis extending through the revolute joint.
2. The imaging apparatus as claimed in claim 1, wherein the gantry is further movable linearly by the stand along at least one horizontal axis and a vertical axis.
3. The imaging apparatus as claimed in claim 1, wherein the gantry is movable linearly by the stand along two horizontal axes standing orthogonally relative to each other.
4. The imaging apparatus as claimed in claim 1, wherein the x-ray radiation detectors are disposed opposite the x-ray radiation sources on the rotor arrangement.
5. The imaging apparatus as claimed in claim 1, wherein a plurality of stationary x-ray radiation detectors complementing one another to form a ring shape is arranged in the gantry.
6. The imaging apparatus as claimed in claim 1, wherein the x-ray radiation detectors comprise different types.
7. The imaging apparatus as claimed in claim 1, wherein one of the x-ray radiation detectors is a receiver consisting of a multiplicity of individual detectors and the other x-ray radiation detector is a planar solid-state x-ray radiation detector.

8. The imaging apparatus as claimed in claim 1, wherein one of the x-ray radiation sources is a carbon nanotube emitter.

9. The imaging apparatus as claimed in claim 1, wherein the rotor arrangement extends through an angle of maximum 270°.

10. The imaging apparatus as claimed in claim 1, wherein the two x-ray radiation sources are arranged offset by 90° from each other.

11. The imaging apparatus as claimed in claim 1, further comprising a patient positioning table that is movable translationally and/or rotatably in space.

12. The imaging apparatus as claimed in claim 11, wherein the patient positioning table is arranged on an articulated-arm robot having at least four degrees of freedom.

13. The imaging apparatus as claimed in claim 12, wherein the articulated-arm robot has six degrees of freedom.

\* \* \* \* \*